United States Patent
Klimcak et al.

[11] Patent Number: 5,610,393
[45] Date of Patent: Mar. 11, 1997

[54] DIODE LASER INTERROGATED FIBER OPTIC REVERSIBLE HYDRAZINE-FUEL SENSOR SYSTEM AND METHOD

[75] Inventors: Charles M. Klimcak, Hawthorne; Gary L. Loper, Huntington Beach; Bernardo Jaduszliwer, Santa Monica, all of Calif.

[73] Assignee: The Aerospace Corporation, El Segundo, Calif.

[21] Appl. No.: 506,279

[22] Filed: Jul. 24, 1995

[51] Int. Cl.$^6$ ........................................................ H01J 5/16
[52] U.S. Cl. .............................. 250/227.14; 250/227.18; 385/143
[58] Field of Search .......................... 250/227.14, 227.18, 250/227.23, 227.21; 356/32–35; 385/12, 14, 123, 145, 143, 126–128

[56] References Cited

U.S. PATENT DOCUMENTS

| | | | |
|---|---|---|---|
| 4,834,496 | 5/1989 | Blyler, Jr. et al. | 250/227.18 |
| 5,315,672 | 5/1994 | Padovani | 385/12 |
| 5,315,673 | 5/1994 | Stetter et al. | 385/12 |

Primary Examiner—Que Le
Attorney, Agent, or Firm—Derrick M. Reid

[57] ABSTRACT

A fiber optical chemical detection system detects the presence of hydrazine fuels and nitrogen tetroxide and nitrogen dioxide gases that are used at rocket launch sites using reversible colorimetric sensors that selectively form chemically reversible, intermolecular charge transfer-complexes with the gases that then absorb laser light communicating through a fiber optic network having a conventional diode laser source transmitting interrogation pulses to a plurality of distributed sensors covering a wide area launch site, the sensor being reactive cladding or distal end types both providing optical reflective returns well suited for reflective near infra-red and visible-red laser interrogation by an optical time domain reflectometry monitor which compares the interrogated laser pulses with sensor returns to determine the contemporaneous extent and location of gas cloud concentration over the distributed wide area.

20 Claims, 3 Drawing Sheets

Intensity-Based Fiber Optic Reversible Sensor Network

Intensity-Based Fiber Optic Reversible Sensor Network

Optical Time Domain Reflectometer Display

Reactive Cladding Hydrazine-Fuel Sensor

Reactive Distal End Hydrazine-Fuel Sensor

Reversible Sensor Calibration Apparatus

DIODE LASER INTERROGATED FIBER OPTIC REVERSIBLE HYDRAZINE-FUEL SENSOR SYSTEM AND METHOD

STATEMENT OF GOVERNMENT

This invention was made with Government support under contract number F04701-88-C-0089 awarded by the Department of the Air Force. The Government has certain rights in the invention.

REFERENCE TO RELATED APPLICATION

The present application relates to applicants' copending patent application entitled Diode Laser Interrogated Fiber Optic Hydrazine-Fuel Sensor System and Method, Ser. No. 08/490,443 filed Jul. 3, 1995. The related application has the same common assignee as the present application. The related application is not prior art to the present application.

FIELD OF INVENTION

The present invention relates to hazardous gas detection sensors, systems and methods. More specifically, the present invention relates to wide area fiber optic hydrazine fuel sensors and networks.

BACKGROUND OF THE INVENTION

Hydrazine and related compounds are used as fuels for space launch vehicles. Hypergolic rocket propellants (hydrazines and nitrogen tetroxide) used in both Air Force and civilian rocket launch operations are extremely hazardous materials whose atmospheric release could present a serious threat to health and the environment. Hydrazine and its methyl-substituted derivatives [methylhydrazine (monomethylhydrazine) and 1,1-dimethylhydrazine (unsymmetrical dimethylhydrazine)], referred to herein as hydrazine-fuels, are flammable toxic substances and suspected carcinogens with current threshold limit values of one hundred to five hundred parts per billion (ppb). The American Conference of Government Industrial Hygienists (ACGIH) has recommended that these exposure limits be lowered to ten ppb for all hydrazines. Similarly, nitrogen dioxide, the spontaneous decomposition product of the oxidizer nitrogen tetroxide, is a hazardous material with a threshold limit value of three ppm. It is imperative that accidental vapor and liquid releases of these materials be rapidly identified and located to minimize exposure of military and civilian personnel and native wildlife to propellant vapor, and to facilitate remedial cleanup operations. Hence, hydrazine fuel vapors are highly toxic, with maximum exposure levels, averaged over eight hours, likely to be set as low as ten parts per billion. Regulatory compliance requires the detection of hydrazine fuel vapors with enough sensitivity to trigger alarms before those exposure levels are reached. Possible sources of hydrazine fuel vapor releases are widely dispersed through launch facilities, which typically span large land areas.

Monitoring of hydrazine fuel vapors is currently accomplished by fixed or portable instruments based on electrochemical sensors or colorimetric chemical indicators. Electrochemical hydrazine-fuel monitors measure electric current produced when a hydrazine-fuel is oxidized in an electrochemical cell, but such monitors are not suitable for monitoring gaseous hydrazine-fuels over wide areas.

Colorimetric monitors use moving paper tapes impregnated with reagents which change color in the presence of hydrazine fuel vapors. Changes in color are automatically detected by photometry. Hydrazine-fuel area monitors using colorimetry have been made by MDA Scientific, Inc. and GMD Systems, Inc. The colorimetric hydrazine-fuel monitors use paper tape impregnated with phosphomolybdic acid (PMA) which moves at a constant rate past an air intake. When exposed to a hydrazine-fuel vapor, the tape changes color. The change in color is detected by comparing light reflected by the tape prior to and after exposure to the air intake. These devices are large, expensive, contain moving parts, require frequent maintenance and are not well suited for systems-oriented operations. Monitors using these sensors are cumbersome, require high maintenance, are not well suited for centralized network operation over a large area and are unable to detect hydrazine fuel vapors below twenty parts per billion.

Another type of colorimetric monitor are the paper cardboard badges which have been used as personal hydrazine-fuel monitors for launch personnel wearing the badges about launch sites. The colorimetric dosimeter badges are used for additional protection. These personnel badges use paper impregnated with reagents. Changes in color indicating exposure to hydrazine fuels are detected visually. The cardboard badges contain pieces of paper impregnated with colorimetric hydrazine-fuel indicators. Usually, more than one indicator is used to provide assurance against false positives. Vanillin, dinitrobenzaldehyde and para-dimethylaminobenzaldehyde are generally used as indicators. The hydrazine-fuel exposure dose is estimated by visually comparing the indicator-impregnated pieces of paper with a color chart. Badges provide only an after-exposure indication of hydrazine-fuel exposure, and in most cases will not help in locating the source of hydrazine fuel vapor leaks.

Fiber optic-based personal dosimeters have been developed. Geo-Centers, Inc. developed a personal hydrazine dosimeter based on an optical fiber chemical optrode. The dosimeter consists of a short length of porous optical fiber impregnated with the colorimetric reagent vanillin. When exposed to hydrazine, vanillin turns yellow by strongly absorbing blue light. The dosimeter operates by absorption with a blue light source, for example, blue light-emitting diode (LED) at one end and a photodetector at the other. Exposure of the fiber to hydrazine causes the transmission of light within the fiber to decrease sharply, and thus reduces the photodetector output signal. This device uses the length of a modified optical fiber incorporating a colorimetric hydrazine indicator as the hydrazine sensor. A disadvantage of this device is that it can not be used to accurately locate a poisonous hydrazine cloud. This device operates by monitoring the light transmitted through the fiber, rather than the backreflected light at a well defined point. Thus, this device is basically a single-sensor device, not compatible with multiple-point detection by laser interrogation. In particular, it can not be interrogated using the Optical Time Domain Reflectometry (OTDR) techniques for multiple-point detection for determining the exact location and extent of a hydrazine-fuel release. The choice of vanillin as a hydrazine indicator dictates that the sensor must be interrogated with blue light, instead of visible red or near-infrared light. The limited use of only blue light has two additional disadvantages which prevent the use of the Geo-Centers sensor in a multiple-point hydrazine-fuel-monitoring network. Firstly, sources of blue light are blue LEDs which typically do not produce sufficient light intensity to interrogate multiple sensors. Secondly, blue light is not transmitted very well by optical fiber which limits severely how far a sensing element can be from the light source and the photodetector. The use of vanillin hydrazine sensors is unsuitable in a multiple point hydrazine-fuel-monitoring network where high intensity illuminating laser light is required to propagate over the wide area.

United States Statutory Invention Registration #H1297, "Detection Device for Hazardous Materials", J. K. Partin and A. Grey, Issued Apr. 5, 1990, describes a fiber optic dosimeter suitable for the detection of hydrazine vapors. It uses evanescent wave absorption in an optical fiber, and uses colorimetric indicator techniques. The reagent used to detect the presence of hydrazine is nitrobenzaldehyde, which is not suitable for interrogation by diode lasers, because after hydrazine exposure, it absorbs light in the blue region of the spectrum, rather than in the visible red or near infra-red. A tungsten/halogen lamp is used but it cannot be pigtailed to an optical fiber and requires the use of an alignment micrometer stage and a focusing lens. The dosimeter detects the presence of hydrazine by absorption, and not by reflection. Thus, this dosimeter cannot be used with optical time domain reflectometry techniques to interrogate the sensor, and the device is only capable of sensing hydrazine at a single point. This dosimeter is not suitable for use in a multipoint fiber optic sensor network. Also, in order to obtain a reference signal measuring how bright the lamp is, the dosimeter detects the red component of the lamp light which propagates through the fiber essentially unattenuated, whether hydrazine is present or not. In order to do so, the dosimeter needs a somewhat complicated detector involving a beam splitter, two interference filters (one for blue light and one for red light), two photodiodes and a second alignment micrometer stage.

U.S. Pat. No. 5,059,790 "Reservoir Fiber Optic Chemical Sensors", Klainer et al., Issued Oct. 22 1991, and U.S. Pat. No. 5,116,759, "Reservoir Chemical Sensors", Klainer et al., Issued May 26 1992, describe a general class of chemical sensors interrogated by optical fibers in which the indicator chemistry takes place in the liquid phase within a special reservoir. The chemical species being sensed enters through a specialized permeable membrane. The selected membrane is for sensing a number of chemical species, amongst which is hydrazine. These systems use a colorimetric indicator general technique. The reagent employed for sensing hydrazine is a cupric neocuproine solution which, upon exposure to hydrazine, absorbs light in the blue region of the spectrum. Optical fibers are only used to convey light in and out of the sensing reservoir. These systems are not suitable for wide area hydrazine detection using a network of distributed sensors adapted for use with conventional visible red and near infra-red lasers.

Evanescent wave fiber optic sensors are well known. Sol-gel glass techniques have been used to make evanescent wave fiber optic chemical sensors. Sol-gel porous glass sensors have been used in medical applications to detect various gases in and the pH of circulating blood. A catheterized optical fiber with a single distal end sensor has been used. These sensors typically use short wavelength blue light lamps for real time interrogation. These sensors have not been adapted to wide area detection of hydrazine-fuels using interrogating lasers.

Most available hydrazine-fuel indicators display changes in the blue wavelength range, for which no convenient laser sources exist, and which is strongly absorbed in optical fibers, rendering hydrazine-fuel optical detection unsuitable for low cost conventional visible red and near infra-red lasers. These hydrazine-fuel detectors are not adaptable to fiber optic networks for detecting hydrazine-fuels over a wide area. Further, previously used colorimetric hydrazine-fuel sensors are irreversible in that once the sensors become exposed to a hydrazine fuel, the sensor permanently remains in an exposure-indicating colorimetric state. Hence, the irreversible colorimetric hydrazine fuel sensor does not indicate the proximal time of exposure and the current hydrazine-fuel concentration, and may no longer be used as an effective sensor after an initial exposure. These and other disadvantages are solved or reduced using the present invention.

SUMMARY OF THE INVENTION

An object of the present invention is to provide a reversible sensor for hydrazine, monomethylhydrazine, or unsymmetrical dimethylhydrazine that is suitable for use with optical fibers.

Another object of the present invention is to provide a reversible colorimetric sensor suitable for interrogation by a diode laser through fiber optics.

Another object of the present invention is to provide a reversible sensor for hydrazine, monomethylhydrazine, or unsymmetrical dimethylhydrazine which is responsive to visible red and near infra-red light illumination.

Yet another object of the present invention is the use of a plurality of hydrazine-fuel reversible sensors disposed at a respective plurality of distal ends of a fiber optic network for detecting contemporaneous concentration of hydrazine, monomethylhydrazine, or unsymmetrical dimethylhydrazine over a wide area.

Still another object of the present invention is the use of a plurality of hydrazine-fuel reversible sensors disposed at a respective plurality of distal ends of fiber optic networks and illuminated by and reflecting laser pulses for detecting the presence of hydrazine, monomethylhydrazine, or unsymmetrical dimethylhydrazine over a wide area using optical time domain reflectometry techniques.

Another object of this invention is to provide a reversible hydrazine fuel fiber optic sensor that employs an electron acceptor reagent that reacts with the hydrazine fuels, which are strong electron donor compounds, to produce a weakly bound intermolecular complex known as an electron donor-acceptor complex that exists in chemical equilibrium with both the hydrazine fuel in the surrounding gas phase and the reagent species in the sensor solid phase and whose concentration in the sensor phase is proportional to the concentration of hydrazine fuels in the surrounding gas phase.

Still another object of this invention is to provide sensors that utilize reversible equilibrium reactions between the electron acceptor, charge-transfer reagents and the hydrazine fuels to form weakly bound electron donor-acceptor complexes in the sensor that possess a new red-shifted absorption band relative to the unreacted charge transfer reagent that permits the complex to be detected via visible red and infrared colorimetric fiber optic techniques including both the distal end reflection and evanescent wave absorption methods.

Still another object of this invention is to provide a method for calibrating the response of a reversible fiber optic distributed sensing system to known concentrations of hydrazine fuel vapor including the temporal responses of the system to both hydrazine fuel introduction and removal at different concentration levels to yield the response rise and recovery times of the fiber optic sensor system.

Still another object of this invention is to provide a reversible nitrogen dioxide fiber optic sensor that employs an electron donor reagent that reacts with nitrogen dioxide, which is a strong electron acceptor compound, to produce a weakly bound intermolecular complex known as an electron donor-acceptor complex that exists in chemical equilibrium with both the nitrogen dioxide in the surrounding gas phase and the reagent species in the sensor solid phase and whose concentration in the sensor phase is proportional to the concentration of nitrogen dioxide in the surrounding gas phase.

Still another object of this invention is to provide a method for calibrating the response of a reversible fiber optic distributed sensing system to known concentrations of nitrogen dioxide vapor including the temporal responses of the system to both nitrogen dioxide introduction and removal at different concentration levels to yield the response rise and recovery times of the fiber optic sensor system.

The present inventions cover a sensor device and fiber optic network that is basically a multiple sensor network for multiple-point detection to assure launch personnel safety, as well as early detection and remediation of hydrazine fuel vapor leaks, in a systems approach, using a network of multiple sensors having adequate sensitivity and dynamic range, deployed through the whole at risk area and transmitting data on hydrazine fuel vapor concentration in real time to a central monitoring facility. The present inventions cover fiber optic sensors and networks that fulfill these requirements. The term hydrazine-fuel(s) as used herein means hydrazine, monomethylhydrazine, and unsymmetrical dimethylhydrazine, in any combination, or separately.

The fiber optic chemical reversible sensor network system detects leaks of toxic vapors or hazardous substances at remote sensor locations during launch operations. The network preferably detects vapors of the hypergolic rocket propellants, but may also be flexible enough to permit incorporation of sensors for other liquids and vapors. The fiber optic system will permit centralized monitoring of numerous sites on a launch complex e.g., fuel and oxidizer storage areas, payload assembly areas, launch vehicle propellant tanks and associated transport lines, personnel areas, base perimeter, aquifers, estuaries, etc. This system will enhance the ability to verify compliance with existing and anticipated environmental regulations and provide rapid identification of the source and strength of accidental propellant releases. Additionally, the system can be used to detect residual propellant vapor emanating from scrubbing towers during normal venting operations.

The fiber optic sensor network system detects hydrazine-fuel vapors. The method employs colorimetric hydrazine-fuel recognition chemistry incorporated within discrete fiber optic sensors located at the distal ends of branches of a fiber optic network. The chemical reaction within the sensors produces a change in absorption and thus a change in the intensity of laser light retro-reflected from the sensors to a receiving photodetector when sufficient hydrazine-fuel vapor has reacted with the colorimetric reagent of the sensors. The sensors may use chemical reagents that react reversibly with hydrazine-fuel vapors to develop hydrazine-fuel vapor concentration sensors that could be deployed in a similar fashion on a remote fiber optic network to detect hydrazine-fuel vapors in the ppb regime.

The present inventions use optical fibers to transmit detection pulses to a plurality of sensors for multiple point detection. The inventive system can interrogate the multiple hydrazine-fuel sensors using the Optical Time Domain Reflectometry technique for multiple-point detection for determining the exact location and extent of a hydrazine-fuel release. Red or near infrared light is used to interrogate the sensors. The network of sensors can be interrogated by red or infrared light, using conventional diode lasers which produce sufficient high light intensities. This light has sufficient intensity to propagate through kilometers of fiber, allowing adaptation of the invention to wide area networks in extended, multiple-point, hydrazine-fuel-monitoring networks.

The sensor of the present inventions includes an identifying colorimetric indicator which, upon reaction with a hydrazine-fuel, would display significant changes in its absorption spectrum in the infra-red and near infrared wavelength range for which reliable, small, low cost diode laser sources are available and for which optimal light propagation through optical fibers obtains. The sensor allows the detection of hydrazine fuel vapors at multiple points over a wide area. Sensors are designed to be interconnected by a fiber optic network, and interrogated by low cost, commercially available diode lasers which operate within the best wavelength range for transmission through optical fibers.

The inventions enable the remote detection of hydrazine fuel vapors at multiple locations with a concentration sensitivity of a few parts per billion. The sensors have cost-effective construction and are less obtrusive than either electrochemical or colorimetric fixed-point monitoring stations. Multiple sensors can be distributed over a wide area and monitored automatically from a single control station. Sensor multiplicity allows mapping of the hydrazine fuel vapor plume and rapid source identification. This approach, allowing real-time surveillance for the presence of hydrazine fuel vapors over a wide area, is inherently safer than after-the-fact reading of personnel exposure badges.

The inventive system works by measuring changes in the intensity of light reflected back by fiber optic colorimetric sensors upon sensor exposure to a hydrazine fuel. Charge transfer reagents are used as the hydrazine-fuel indicator preferably immobilized either in a porous glass matrix which may be prepared by the sol-gel technique, or a polymer matrix like polyvinyl acetate. The sensors may have different configurations including an evanescent wave fiber optic colorimetric reactive cladding hydrazine-fuel sensor or a fiber optic reactive distal end hydrazine-fuel sensor. The sensors are reversible in that during exposure, the sensor obtains an exposed state, but after exposure, returns to an initial state, thereby indicating the contemporaneous concentration of a gas, rather than past exposure. Hence, the reversible sensors indicate the presence of the gas to be detected and can be used continuously during several exposure episodes. During exposure to hydrazine fuel vapors, the matrix undergoes a change in absorptivity of red or infrared light. In the absence of the hydrazine fuel vapors, the sensors revert back to their original absorptivity indicating the absence of the hydrazine fuel vapors.

One or more sensors are optically coupled to a fiber optic line, and interrogated by red or infrared light pulses produced by inexpensive diode lasers. The back-reflected pulses may be detected using the Optical Time Domain Reflectometry (OTDR) technique. For example in its unexposed state, a sensor could be designed to reflect back most of the incoming light, and in its exposed state, to reflect less light. Alternatively, a sensor could be designed to reflect more light in its exposed state and less light in its unexposed state. The change in the fraction of light reflected back measures the hydrazine-fuel concentration absorbed by the sensor, and calibration experiments allow the derivation of the concentration from the change in sensor reflectivity. The sensitivity can be adjusted by varying the reagent concentration, and a combination of sensors having different sensitivities can provide measurement capabilities over very large dynamic ranges.

The fiber optic sensor's specific design enables integration in a fiber optic sensing network to detect contemporaneous concentrations of hydrazine-fuel or nitrogen dioxide vapors at multiple points, and is particularly well suited for interrogation using the OTDR technique. The electron acceptor charge transfer reagent is used as a hydrazine-fuel colorimetric indicator in conjunction with interrogation of the sensors by diode lasers emitting near infrared or red light pulses. The electron donor charge transfer reagent is used as a nitrogen tetroxide and nitrogen dioxide colorimetric indicator in conjunction with interrogation of the sensor by diode lasers emitting near infrared or visible red light pulses. Pigtailed lasers can be coupled to fiber very easily, and red or infrared light absorption within the fiber is very low. Other, commonly used colorimetric indicators for hydrazine fuels must be interrogated with shorter wavelength light, requiring the use of lasers which are much more expensive, much larger, more difficult to couple to optical fiber and less reliable than diode lasers. Additionally, at those shorter wavelengths light does not propagate through optical fibers as efficiently. During exposure spectral reflectivity changes are well suited for use in a fiber optic network communicating infra-red and near infrared wavelengths. A porous glass or polymer matrix impregnated with a charge transfer reagent is used as a reactive cladding or distal termination in the reversible sensors. These combinations of matrix, colorimetric reagent, and configuration result in gas concentration sensors having very high sensitivity. These and other advantages will become more apparent in the following detailed description of the preferred embodiment.

DETAILED DESCRIPTION OF THE PREFERRED EMBODIMENT

Figure 1:
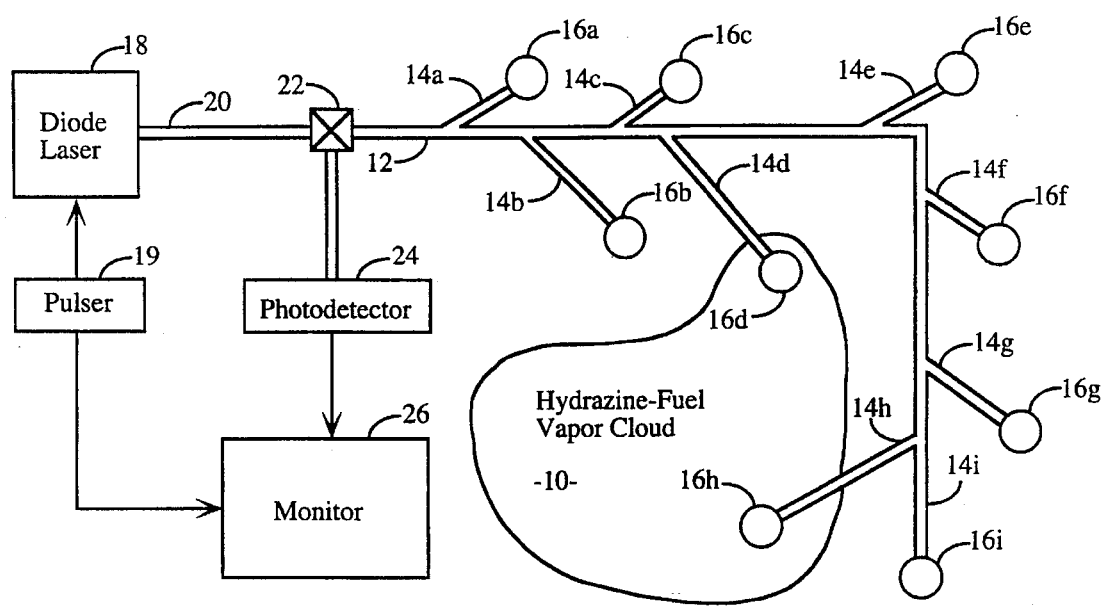
FIG. 1 is a block diagram of an intensity based fiber optic reversible sensor network.
Figure 2:
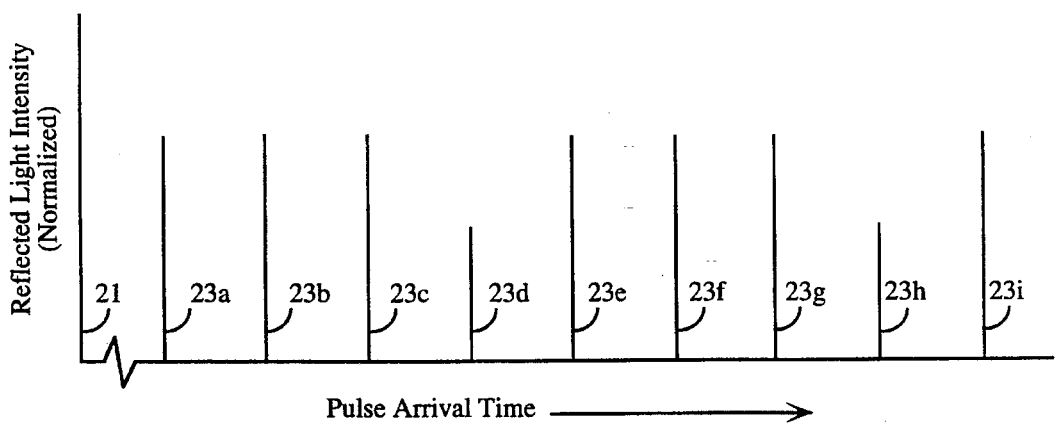
FIG. 2 is graph of an optical time domain reflectometer display of reflected laser pulses in an intensity based fiber optic reversible sensor network.

Referring to FIGS. 1 and 2, an intensity-based fiber optic chemical sensor network system is shown in FIG. 1 and is used for the remote detection of hydrazine-fuel propellant vapor clouds 10 which may leak from rocket-launched space vehicles and emergency power units used in airplanes. The fiber optic chemical sensor network system is used for the remote detection of toxic rocket propellant vapors, such as hydrazine and its derivatives, as well as nitrogen tetroxide and its spontaneous decompostion product nitrogen dioxide which may be present at Air Force and civilian rocket launch sites. The system uses one or more fiber optic networks 12 which typically includes a fiber split into a plurality of fiber optic branches 14a–i each having at each of its respective distal ends a respective fiber optic colorimetric sensor 16a–i that selectively reacts reversibly with the propellant vapors 10 to yield chemical compounds within the sensors 16 that absorb laser light communicated from a laser 18 through the fiber optic 12 and branches 14 to sensors 16. The sensors 16 reflect laser light pulses having intensities dependent upon the present contemporaneous concentration of the hydrazine fuel. The system includes a pulser 19 for activating the laser 18 and providing an optical reference, an optical trunk 20 for receiving a laser pulse 21 from the laser 18, an optical coupler 22 for communicating the laser pulse 21 into the fiber optic network 12 and for communicating reflected pulses 23a–i respectively from sensors 16a–i to a photodetector 24 communicating corresponding electrical pulses to a monitor 26 which compares the reflected pulses 23 to the laser pulse 21 by reference to the pulser 19. By time domain reflectometry analysis, the present contemporaneous concentration of the hydrazine fuel can be determined as well as the time-integrated exposure. As shown, detectors 16d and 16h of FIG. 1 are exposed to the hydrazine fuel vapor cloud 10 and the corresponding reflected pulses 23d and 23h of FIG. 2 have attenuated amplitudes.

Remote detection of the hydrazine-fuel vapor 10 in the few parts per billion (ppb) concentration regime may be realized by a network having a fiber 12 that may be, for example, one kilometer in length and used with a low power ten milliwatt diode laser 18. The fiber optic sensor network may be expanded to have many fibers 12 in a multiplexed system containing hundreds of branches 14 and sensors 16 for vapor detection over a plurality of wide areas. The performance of a field-scale remote fiber optic detection network is enhanced by discrete chemical vapor sensors 16, optical fibers 12 and branches 14 connected in a variety of ways including serial, parallel, or hybrid serial/parallel topologies to provide flexibility for detection over many different predetermined wide areas which may have complex three-dimensional topography.

The sensors 16 are interconnected by a fiber optic network 12. The laser 18 is the preferred light source because it can provide an intense light source emitted in one direction into the optical fiber network 12 for high illumination efficiency. The laser 18 interrogates the sensors 16 at distal ends of the several branches 14 of the fiber network 12. The network 12 can be kilometers in length. The diode laser 18 provides a high population of electron-hole pairs providing cascaded photoemissions which become a laser pulse 21 of monochromatic light centered about a predetermined wavelength characteristic of the electron-hole pairs. The diode laser 18 preferably provides near infrared light between 700–1600 nm or visible light between 650–700 nm. Visible red and near infrared light wavelengths are efficiently transmitted during propagation without serious degradation along the length of the optical fiber network 12 by absorption by the optical fibers 12. Preferred wavelengths between 650 and 1600 nm correspond well to available inexpensive commercial laser diodes, as well as efficient light transmission through the fiber optics.

The operation of the system starts with a short pulse of laser light 21, preferably at about ten nanoseconds from, a visible or near infrared, diode laser 18 communicated into the fiber optic trunk line 20 that transmits the laser pulse 21 to hydrazine-fuel sensors 16 located at numerous distal points within a launch complex. The laser light pulse 21 is retro-reflected from these sensors 16 as reflected pulses 23 which are detected by the photodetector 24 which may be a photomultiplier tube and displayed by the monitor 26 which may be an optical time domain reflectometer operating in a return loss mode to yield a plot of the returned light intensity versus its arrival time at the photodetector as shown in FIG. 2.

The concentrations over time of hydrazine fuel measured by the sensors are determined from the intensity of the returned light pulses while identification of the sensors is determined by the pulse arrival time order. For example, the fourth and eighth return light pulses 23d and 23h in the trace of FIG. 2 exhibit reduced intensity relative to the other pulses due to the close proximity of the fourth and eighth sensor to the depicted hydrazine-fuel vapor cloud 10.

To assess the feasibility of deploying a field-scale one kilometer sensor network, a parametric computer model of a multimode fiber optic sensor network may be used. This model incorporates all pertinent aspects of detection including laser power, wavelength, propagation losses, coupler insertion losses, sensor responsivity, photodetector responsivity, intrinsic photodetector noise, photon statistical noise, laser intensity referencing, electronic bandwidth, multimodal and material dispersion, desired spatial resolution, and sensor/dosimeter deployment topology (i. e., serial, parallel, hybrid serial/parallel). One such model indicates that a five percent change in the return signal level from an individual sensor could be observed with a fiber optic network composed of one hundred sensors 16 in a parallel star configuration, having a trunk length of one kilometer using a ten milliwatt 680 nanometer diode laser 18. Although laboratory measurements are easily capable of detecting much smaller intensity changes, a field device that triggers warnings at fractional intensity changes less than five percent may increase false alarm rates. The computed signal to noise ratio on the returned light signal with direct detection is one hundred with this exemplar system, yielding a signal to noise ratio of five on the observed five percent change level.

Referring to FIGS. 1, 2, 3 and 4, preferably the sensors 16 are fabricated by dispersing a charge transfer reagent within either a porous cladding or a porous distal end coating, that is, prepared by a low temperature sol-gel technique. Several recognition chemistries for hydrazine-fuel detection may be used. Chemical detection is based on the selective reaction of a hydrazine fuel with a colorimetric reagent to produce a compound that absorbs the laser light pulse 21. The preferred choice for a sensor 16 to be used in a wide-area fiber optic hydrazine-fuel vapor sensor system would be a reversible fiber optic sensor 16. Such a sensor 16 could utilize reversible chemical reaction that occur between hydrazine fuels and a suitable chemical charge transfer reagent immobilized on the sensor 16 to form a colorimetrically detectable reaction product in the sensor 16 whose concentration is proportional to the concentration of hydrazine fuel 10 in the gas phase in close proximity to the sensor 16. Removal of the hydrazine fuel 10 from the surrounding gas phase of the reversible sensor 16 would result in dissociation of the reaction products, thus restoring the colorimetric response of the sensor 16 to the response that it exhibited prior to its exposure to the hydrazine fuels. Chemical reagents that undergo reversible reactions with the hydrazine fuels are required for its manufacture. Electron-acceptor compounds are one class of compounds that could be used to manufacture a reversible sensor for use with the hydrazine fuels. The hydrazine fuels are strong electron donor compounds. Electron acceptor compounds form intermolecular charge-transfer complexes with the hydrazine fuels that dissociate upon removal of the hydrazine-fuel vapor. The formation of such an intermolecular charge-transfer complex is accompanied by the formation of a new electronic absorption band. The new charge-transfer band possesses absorption at longer wavelengths than the absorption bands for the donor hydrazine fuel species or acceptor species in their uncomplexed states. In the reversible sensor 16 based on the formation of an intermolecular complex between a hydrazine-fuel and an electron acceptor, there would exist a chemical equilibrium between the concentration of the hydrazine fuel in the gas phase in the proximity of the sensor 16 and the amount of molecular complex formed in the sensor 16. The existence of an equilibrium relationship between the hydrazine fuel that is associated in the molecular complex and the free hydrazine fuel in the surrounding gas phase ensures that any reduction in the hydrazine-fuel concentration in the gas phase will be accompanied by a proportionate reduction in the concentration of the molecular complex and a concomitant reduction in the response of the sensor 16, thus indicating the presence of the lowered hydrazine-fuel concentration in the surrounding vapor.

In one embodiment, the sensors are fabricated with organic or inorganic electron acceptor charge transfer reagents immobilized within either sol-gel or polymer matrices that can be coated on silica fibers for the purpose of detecting the concentration of hydrazine fuel vapors. The organic charge transfer reagents are aromatic or olefinic molecules containing strong electron withdrawing groups [e.g. —CN, —$NO_2$, —$CF_3$, —F, —Cl, —Br, —I, —$CO_2H$, —$CO_2Na$, —$SO_3H$, —$SO_3Na$] that can accept electrons donated by the hydrazine fuels resulting in the formation of weakly bound intermolecular charge transfer complexes. Examples of organic classes of molecules that meet these requirements are nitro-and cyano-substituted quinones, including napthoquinones and anthraquinones, cyanines, including phthalocyanines and naphthalocyanines, and organometallic complexes such as dithiolenes. The inorganic, electron acceptor, charge-transfer reagents are transition metal compounds that contain unoccupied molecular orbitals that accept electrons donated by hydrazine fuels resulting in the formation of a weakly bound intermolecular charge transfer complex.

Similarly, the reversible fiber optic sensor 16 would be the preferred choice for a sensor to be used in a wide-area fiber optic nitrogen tetroxide or nitrogen dioxide vapor sensor system. This sensor would employ reversible chemical reactions that occur between nitrogen dioxide, the spontaneous decomposition product of nitrogen tetroxide, and a suitable chemical reagent immobilized on the sensor to form a colorimetrically detectable reaction product in the sensor whose concentration is proportional to the concentration of nitrogen dioxide in the gas phase near the sensor. Removal of nitrogen dioxide from the surrounding gas phase of this reversible sensor would result in dissociation of the reaction products and restore the response of the sensor to that exhibited prior to its exposure to nitrogen dioxide. Electron-donor compounds are one class of compounds that could be used to manufacture a reversible sensor for detecting nitrogen dioxide. Nitrogen dioxide is a good electron acceptor compound and can reversibly form intermolecular charge-transfer complexes with strong electron-donor compounds. Such a complex would possess a new electronic absorption band with longer wavelength absorption than the bands in uncomplexed donor and acceptor (nitrogen dioxide) species. In a reversible sensor based on the formation of these complexes, there would exist a chemical equilibrium between the concentration of nitrogen dioxide in the gas phase in the proximity of the sensor and the amount of molecular complex formed in the sensor. The existence of an equilibrium relationship between the nitrogen dioxide that is associated in the molecular complex and the free nitrogen dioxide in the surrounding gas phase ensures that any reduction in the nitrogen dioxide concentration in the gas phase will be accompanied by a reduction in the concentration of the molecular complex and a concomitant reduction in the response of the sensor, thus indicating the presence of the lowered nitrogen dioxide concentration in the surrounding vapor.

In another embodiment, the sensors are fabricated with organic or inorganic electron donor charge transfer reagents immobilized within either sol-gel or polymer matrices that can be coated on silica fibers for the purpose of detecting the concentration of nitrogen dioxide vapors. The organic charge transfer reagents are aromatic or olefinic molecules containing strong electron donating groups [e.g. $-CH_3$, $-OCH_3$, $-NH_2$, $-NH(CH_3)$ $-N(CH_3)_2$] that can donate electrons accepted by nitrogen dioxide resulting in the formation of weakly bound intermolecular charge transfer complexes. Examples of organic classes of molecules that meet these requirements are methyl- and dimethylamino-substituted mono- and polycyclic aromatics including benzenes, naphthalenes, and anthracenes. The inorganic, electron donor, charge-transfer reagents are transition metal compounds that contain occupied molecular orbitals that donate electrons accepted by nitrogen dioxide resulting in the formation of a weakly bound intermolecular charge transfer complex. The sensors utilize reversible equilibrium reactions between the electron donor, charge-transfer reagents and nitrogen dioxide to form weakly bound electron donor-acceptor complexes in the sensor that possess a new red-shifted absorption band relative to the unreacted charge transfer reagent that permits the complex to be detected via visible red and infrared colorimetric fiber optic techniques including both the distal end reflection and evanescent wave absorption methods.

The spectral wavelength changes of reflected light of chemical reagent after exposure are between 500 nm to 1600 nm. The reflectivity spectrum is derived from separate measurements of the reflection spectra of unexposed and exposed sensors. The action spectrum is defined as the change in reflectivity caused by exposure to hydrazine fuel vapor divided by the unexposed reflectivity. The action spectrum occurs over an ideal wavelength range accessible with visible and near infrared diode lasers. The reaction between a hydrazine fuel and charge transfer reagent is reversible and thus suitable for use as a concentration sensor and a time- integrated dosimeter sensor. The sensor 16 contains the immobilized charge transfer reagent used to detect the contemporaneous concentration of a hydrazine fuel or nitrogen dioxide or nitrogen tetroxide oxidizers. Standard acid-catalyzed sol-gel coating techniques may be used for reagent immobilization using procedures similar to those used in fiber optic chemical sensor construction and manufacture. As examples, both reactive cladding sensors and distal end sensors 16 may be constructed.

Figure 3:
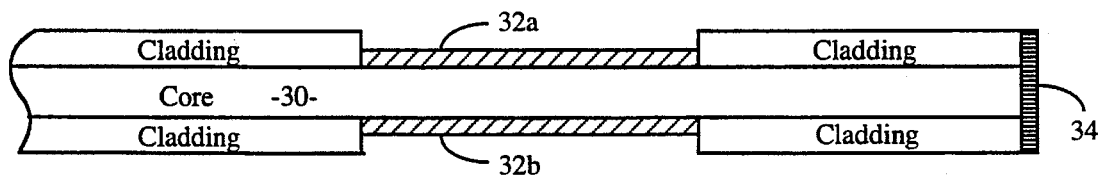
FIG. 3 depicts an evanescent wave fiber optic reactive cladding hydrazine-fuel reversible sensor coupled to an optical fiber network and having a fiber core, fiber cladding, charge transfer reagent impregnated matrix reactive cladding with a high reflectivity termination.

Referring to FIG. 3, a reactive cladding may be produced from a sol having a $H_2O:Si$ molar ratio of six. A mixture of fifty-two ml tetra-ethylortho-silicate, one-hundred ml ethanol, and twenty-five ml 0.1N HCl is sonicated in a Parafilm sealed vessel for seventeen hours at 50° C. in a ultrasonic bath. The charge transfer reagent (CTR) is then added to this precursor sol at the required concentration. Reactive cladding sensors are fabricated preferably from high OH TECS (a Trademark of 3M Company) Hard Clad step index silica fiber having a core 30 with a core diameter of two-hundred microns. Ten cm of cladding near the end of an optic branch may be removed by rubbing with an acetone-dampened lens tissue. The de-clad fiber 32a–b should be immersed in hot, 60° C., Chromerge for thirty minutes, rinsed with copious amounts of deionized water and microscopically inspected for residual cladding. The de-clad region 32 is then re-immersed in hot Chromerge for an additional thirty minutes, rinsed with water, and immersed in the CTR/Sol precursor solution. The region 32 should be allowed to remain in the solution for thirty minutes before withdrawing it at a rate of 10 cm/minute into a sealed chamber. The coated fiber should be first dried in ethanolic air in this chamber for forty hours. The coated fiber should then be dried in an oven under an air atmosphere at 70° C. for twenty hours. Detection with the reactive cladding sensors relies on evanescent wave coupling of the laser light propagating through the sensor region 32. Epoxy 34 should be applied to the cleaved distal end of the reactive cladding sensor to shield the silica surface from hydrazine fuel or nitrogen dioxide vapor and to provide a stable retro-reflected intensity from the silica/epoxy interface. The intensity of the reflection can be considerably enhanced (by four times that of a freshly cleaved fiber) if the epoxy coating is formed with a rounded surface of the appropriate shape. Alternatively, one could deposit a reflective metal, such as a silver coating on the distal surface to produce high retro-reflected intensity.

Figure 4:
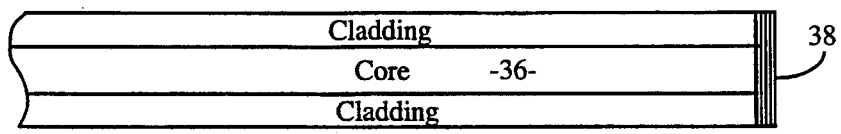
FIG. 4 depicts a fiber optic reactive distal end hydrazine-fuel reversible sensor coupled to an optical fiber network and having a fiber core, fiber cladding and a charge transfer reagent impregnated matrix reactive distal termination.

Referring to FIG. 4, a distal end coated sensor may be produced with a sol having a $H_2O:Si$ ratio of two that is prepared. Fifty-two ml tetraethylorthosilicate, 6.3 ml water, thirty-nine ml ethanol, and 2.5 ml of 1.0 N HCl is mixed and sonicated in a Parafilm sealed vessel for twenty hours at 50° C. in an ultrasonic bath. The sol's liquids are then allowed to evaporate in an open vessel until the sol's viscosity, at ten cp, is sufficient for producing an end coated sensor. The charge transfer reagent is added to this precursor sol at the required concentration. The distal end sensor 38 is then attached to the end of Spectran graded index silica/silica fiber having a core 36 with a fifty micron core diameter and a communications bandwidth of 1.2 GHz-km at 850 nm. A dip-coating and drying procedure is used to produce the distal end 38 sensor which is similar to that used for the active region 32 of reactive cladding sensor. Reflections at the silica/sol-gel and sol-gel/air interfaces provides the retro-reflected return light pulse from the sensor. The retro-reflected intensity should be continuously monitored during all drying and epoxying operations to observe the occurrence of any catastrophic failures due to sol-gel cracking.

Figure 5:
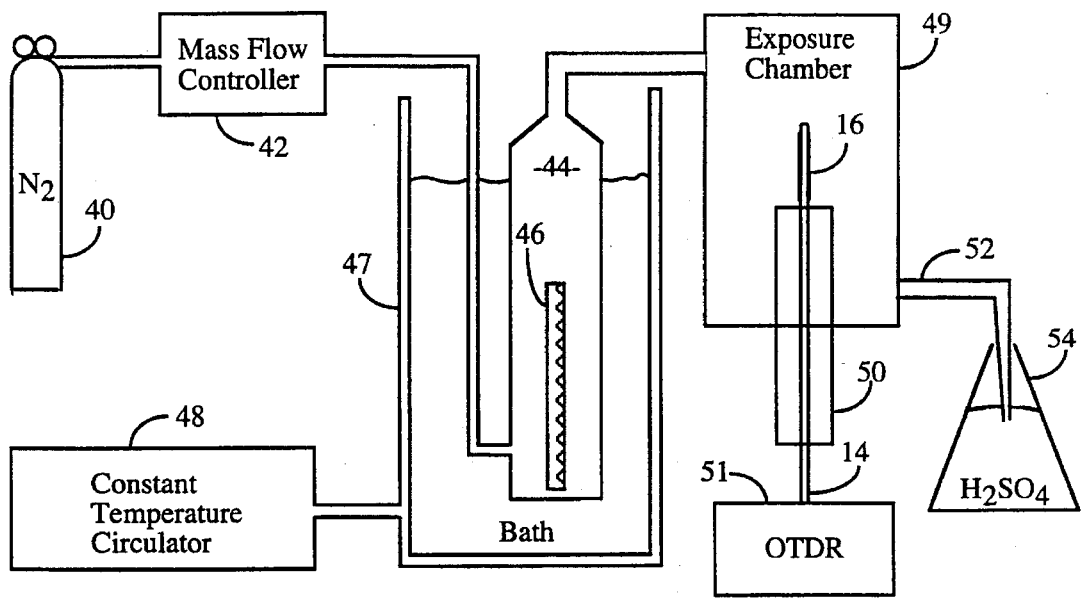
FIG. 5 is a schematic diagram of a hydrazine-fuel reversible sensor verification and calibration apparatus.
Figure 6:
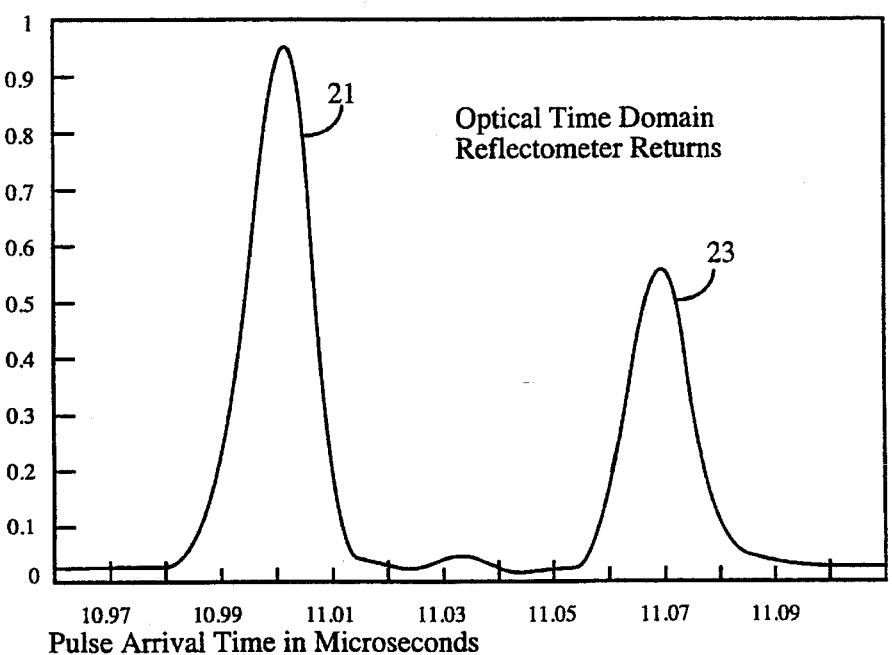
FIG. 6 is a graph depicting optical time domain reflectometer returns of sensor signals.

Referring to FIGS. 5 and 6, calibration of the sensor response to a hydrazine fuel vapor may be performed prior to use in a distributed network. A calibration system may include a flow source 40 of $N_2$ gas at an actively regulated flow rate of 200 ml/min by a mass flow controller 42 for delivery of $N_2$ into a thermostated mixing vessel 44 containing a hydrazine-fuel permeation tube 46. Hydrazine-fuel permeation tubes are manufactured by Kintek Laboratories of La Marque, Tex., for example, that emit a low flux (typically 100 ng/min) of hydrazine-fuel vapor into a mixing vessel 44. The vessel 44 is disposed in a circulating bath 47 controlled by a constant temperature circulator 48 which maintains the bath 47 at a constant temperature preferably at 25° C. Gaseous mixtures of nitrogen and the hydrazine-fuel in the mixing chamber 44 are then directed into a sensor exposure chamber 49 whose surfaces have been coated with paraffin in order to minimize parasitic losses of hydrazine-fuel vapor to the walls. A hydrazine fuel sensor 16 is disposed at the end of a optic fiber 14 which is protected by a sleeve 50 which is fed through and into the exposure chamber 49. The length of the optic fiber 14 may be equal to the length as used in a network to be installed, including all other attached serial and parallel fibers 14 and sensors 16, not shown, so as to provide a exact working configuration for purposes of sensor calibration. Alternatively, a sensor may be calibrated using a predetermined length of branch optic fiber, and the calibration adjusted to account for fiber line losses that are predicted in an actual configuration to be installed. The optical time domain reflectometer 51 is used to calibrate the sensor 16. The reflectometer 51 would include a laser 18, trunk line 20, pulser 19, coupler 22, photodetector 24, 12 and monitor 26 as shown in FIG. 1. The reflectometer 51 measures return time displacements and amplitudes at various exposures. The mixing vessel 44 typically provides a preferred average hydrazine-fuel vapor concentration in the exposure chamber 49 of two-hundred ppb of the hydrazine fuel in nitrogen carrier gas. Hydrazine fuel vapor flowing from the chamber 49 can be collected by bubbling the effluent vapor through a small tube 52 into a vessel 54 containing 0.1N sulfuric acid. A measured amount of the collected sulfuric acid sample may be analyzed using standard spectrochemical techniques employing colorimetric reagents to determine the average concentration of the hydrazine fuel in the chamber 49 during the collection and exposure periods. For example, Hydraver 2, manufactured by Hach Company, may be used as a colorimetric reagent for hydrazine. A known quantity of reagent is added to a measured amount of acid solution to provide a solution that changes color upon exposure to hydrazine vapor. The color developed may be compared for colorimetric match to solutions containing known quantities of hydrazine and the reagent to determine the concentration of hydrazine in the gas stream. The reflectometer records the amplitude attenuation produced in the fiber optic sensor which is then calibrated to the amount of hydrazine exposure. Analogous procedures can be used for calibrating the sensor response to nitrogen dioxide vapor prior to use in a distributed network.

The gas flow system used to calibrate sensors is also capable of determining sensor rejection against potential interferences such as $H_2O$, $NH_3$, organic solvents, ozone, and other physical influences, for example, temperature, pressure, vibration and sensor aging. The preferred electron acceptor compound for a hydrazine fuel is 2,4,7-trinitrofluorenone with a corresponding laser interrogating wavelength of between 630 and 900 nm. The preferred electron donor compound for both nitrogen dioxide and nitrogen tetroxide is N, N, N', N' tetramethylpara-diphenylenediamine with a corresponding laser interrogating wavelength of between 630 and 900 nm. While the preferred sensor is a charge-transfer-reagent-based colorimeter sensor, various sensor structures, systems and method modifications and improvements may improve gas detection. Those improvements and modifications may nonetheless fall within the spirit and scope of the following claims.

We claim:

1. A reversible sensor for optical absorption and reflection of an interrogating optical pulse communicated through an optical fiber having an opaque tube and a transparent core, said reversible sensor comprises:

an optical fiber end at a core end of said core of said optical fiber, an electron charge transfer reagent that forms intermolecular complex with a gas, said intermolecular complex associates during exposure to said gas and complex rapidly dissociates in the absence of said gas, said intermolecular complex association and disassociation is characterized by changing said optical absorption and reflection of said optical pulse causing amplitudinal changes of said optical pulse when reflected back through said optical fiber, and a medium integrally formed with said core end and for containing said reagent.

2. The reversible sensor of claim 1 wherein said electron charge transfer reagent is an electron acceptor compound, said gas is a hydrazine fuel, and said sensor is for detecting contemporaneous exposure concentration of said hydrazine fuel.

3. The reversible sensor of claim 1 wherein said electron charge transfer reagent is an electron donor compound, said gas is nitrogen dioxide, and said sensor is for detecting contemporaneous exposure concentration of nitrogen dioxide.

4. The reversible sensor of claim 1 wherein said optical fiber is cladded and said medium is porous glass longitudinally and integrally formed at an uncladded end region of said optical fiber end.

5. The reversible sensor of claim 1 wherein said medium is porous glass disposed at a distal end of said optical fiber end.

6. The reversible sensor of claim 1 wherein said optical pulse is a laser pulse having a wavelength between 650 and 1600 nanometers.

7. A system for detecting contemporaneous exposure of a gas over a wide area, said system comprising:

a diode laser means for generating a laser pulse, a fiber optic network of optical fibers comprising opaque tubes and transparent cores connected to said diode laser means for communicating said laser pulse distributed within said wide area, a plurality of reversible sensor means distributed within said wide area for receiving said laser pulse and for absorbing and reflecting said laser pulse to provide a respective plurality of reflected returns amplitudinally changed by said plurality of reversible sensor means when reacting to said contemporaneous exposure of said gas through changes in optical absorption and reflection of said laser pulse by an electron charge transfer reagent disposed in said plurality of reversible sensors means, and a monitor means connected to said fiber optic network for receiving said plurality of reflected returns correlated to said respective plurality of reversible sensor means and for determining which ones of said plurality of reversible sensor means are contemporaneously exposed to said gas within said wide area.

8. The system of claim 7 wherein said laser pulse has a wavelength between 650 and 1600 nanometers.

9. The system of claim 7 wherein said gas is a hydrazine fuel, and said electron charge transfer reagent is an electron acceptor compound.

10. The system of claim 7 wherein said gas is a hydrazine fuel and said electron charge transfer reagent is a 2,4,7-trinitrofluorenone electron acceptor compound.

11. The system of claim 7 wherein said electron charge transfer reagent is an electron donor compound.

12. The system of claim 7 wherein said gas is nitrogen dioxide and said electron charge transfer reagent is a N, N, N' N' tetramethylpara-diphenylenediamine electron donor compound.

13. The system of claim 7 wherein said gas is nitrogen tetroxide and said electron charge transfer reagent is a N, N, N' N' tetramethylpara-diphenylenediamine electron donor compound.

14. The system of claim 7 further comprising fiber optic trunk means connected to said diode laser means for communicating said laser pulse to said fiber optic network, a pulser means for providing a reference pulse communicated to said diode laser means for activating said diode laser means to generate said laser pulse, said reference pulse further communicated to said monitor means for providing a time reference of said laser pulse, and a fiber optic coupler means connected between said fiber optic network and said fiber optic trunk means for communicating said laser pulse from said fiber optic trunk means to said fiber optic network and for communicating said plurality of reflected returns to said monitor means.

15. The system of claim 7 wherein said fiber optic network comprises an optical fiber having a plurality of fiber optical branches extending from said optical fiber at a plurality of points along said optical fiber, said plurality of optical fiber branches have said respective plurality of reversible sensor means located at respective distal ends of said optical fiber branches.

16. A method for detecting contemporaneous concentration exposure of a gas over a wide area, said method comprising steps of:

generating a laser pulse, distributing a laser pulse through a distributive fiber optic network of optical fibers comprising opaque tubes and transparent cores to a plurality of distal end reversible sensors having an electron charge transfer reagent for absorbing said laser pulse and reflecting returns dependent upon contemporaneous concentration to said gas, receiving said returns, determining respective time displacements from said generation step until said receiving step for said returns, correlating said returns to said reversible sensors dependent on said time displacements, correlating said returns to respective ones of said reversible sensors by time displacement from said generating step to said receiving step, measuring amplitudinal changes of said returns caused by said contemporaneous concentration exposure to said gas, and determining the extent of said contemporaneous concentration exposure of said sensors disposed at respective points within said wide area.

17. The method of claim 16 wherein said laser pulse has a wavelength between 650 and 1600 nanometers, said gas is a hydrazine fuel, and said electron charge transfer reagent is an electron acceptor compound.

18. The method of claim 16 wherein said gas is nitrogen dioxide, said electron charge transfer reagent is an electron donor compound.

19. The method of claim 16 wherein said gas is nitrogen tetroxide, and said electron charge transfer reagent is an electron donor compound.

20. The method of claim 16 further comprising steps of, measuring amplitudes of said returns for said reversible sensors absent contemporaneous exposure to said gas, exposing said reversible sensors to a calibration concentration of said gas, measuring said calibration concentration, measuring amplitudinal changes of said returns correlated to said calibration concentration, and calibrating said reversible sensors to said calibration concentration correlated to said amplitudinal changes.

* * * * *